United States Patent
Saue (10) Patent No.: US 11,433,152 B2
(45) Date of Patent: Sep. 6, 2022

(54) ELECTROCHEMICAL DEVICE FOR RELEASING IONS

(71) Applicant: NMR TECHNOLOGY AS, Bønes (NO)

(72) Inventor: Vidar Saue, Bønes (NO)

(73) Assignee: NMR Technology AS, Bønes (NO)

( * ) Notice: Subject to any disclaimer, the term of this patent is extended or adjusted under 35 U.S.C. 154(b) by 0 days.

(21) Appl. No.: 17/035,426

(22) Filed: Sep. 28, 2020

(65) Prior Publication Data

US 2021/0060194 A1 Mar. 4, 2021

Related U.S. Application Data

(62) Division of application No. 15/533,160, filed as application No. PCT/EP2015/078782 on Dec. 7, 2015, now abandoned.

(30) Foreign Application Priority Data

Dec. 5, 2014 (EP) ...................................... 14196595

(51) Int. Cl.
*C25B 15/02* (2021.01)
*A61L 2/14* (2006.01)
(Continued)

(52) U.S. Cl.
CPC .................. *A61L 2/14* (2013.01); *A46B 9/04* (2013.01); *A46B 15/0008* (2013.01);
(Continued)

(58) Field of Classification Search
CPC ........... C25B 15/02; C25B 9/65; C25B 15/00; C25B 9/17; C25B 9/00; C25B 15/08
See application file for complete search history.

(56) References Cited

U.S. PATENT DOCUMENTS

| 4,726,826 A | 2/1988 | Crawford et al. |
| 10,111,805 B2 | 10/2018 | Park et al. |

(Continued)

FOREIGN PATENT DOCUMENTS

| CN | 103813831 A | 5/2014 |
| JP | 2001190336 | 7/2001 |

(Continued)

OTHER PUBLICATIONS

Partial Translation of Japanese Office Action issued in related patent Application No. 2017-529837 dated May 28, 2019 (p. 3).

*Primary Examiner* — Zulmariam Mendez
(74) *Attorney, Agent, or Firm* — Knobbe Martens Olson & Bear LLP (57) ABSTRACT

The present invention relates to an electrochemical device for releasing ions, comprising an electrical circuit comprising a first electrode and a second electrode adapted for providing a galvanic cell when the electrodes are exposed to a fluid constituting an electrolyte, and a boost converter adapted for amplifying a potential generated between the first and the second electrode. The electrical circuit further comprises a third electrode connected with an output side of the boost converter, wherein the second and the third electrode constitutes an electrolytic cell powered by the galvanic cell when the electrodes are exposed to a fluid. The present invention further relates to devices, such as a toothbrush or a shaver, adapted for being used in connection with a fluid, comprising such electrochemical device for releasing ions.

17 Claims, 6 Drawing Sheets

(51) Int. Cl.

| | | |
|---|---|---|
| *A46B 15/00* | (2006.01) | |
| *A61C 17/34* | (2006.01) | |
| *A61C 17/20* | (2006.01) | |
| *A61L 2/03* | (2006.01) | |
| *C02F 1/46* | (2006.01) | |
| *A61N 1/30* | (2006.01) | |
| *A61N 1/32* | (2006.01) | |
| *A46B 9/04* | (2006.01) | |
| *A61N 1/04* | (2006.01) | |
| *A61N 1/26* | (2006.01) | |
| *A61N 5/06* | (2006.01) | |
| *B26B 21/40* | (2006.01) | |
| *B65D 41/00* | (2006.01) | |
| *C02F 1/461* | (2006.01) | |
| *H02M 3/335* | (2006.01) | |
| *C02F 1/32* | (2006.01) | |
| *A61L 2/00* | (2006.01) | |
| *A61N 1/22* | (2006.01) | |
| *A61L 2/10* | (2006.01) | |
| *A61N 1/378* | (2006.01) | |
| *B26B 21/22* | (2006.01) | |

(52) U.S. Cl.
CPC ...... *A46B 15/0024* (2013.01); *A46B 15/0034* (2013.01); *A61C 17/20* (2013.01); *A61C 17/3481* (2013.01); *A61L 2/035* (2013.01); *A61N 1/0432* (2013.01); *A61N 1/26* (2013.01); *A61N 1/30* (2013.01); *A61N 1/306* (2013.01); *A61N 1/325* (2013.01); *A61N 5/0624* (2013.01); *B26B 21/405* (2013.01); *B26B 21/4087* (2013.01); *B65D 41/00* (2013.01); *C02F 1/4606* (2013.01); *C02F 1/46109* (2013.01); *C02F 1/46176* (2013.01); *H02M 3/335* (2013.01); *A46B 2200/1073* (2013.01); *A61L 2/0011* (2013.01); *A61L 2/10* (2013.01); *A61L 2202/11* (2013.01); *A61N 1/22* (2013.01); *A61N 1/322* (2013.01); *A61N 1/3785* (2013.01); *A61N 2005/0606* (2013.01); *A61N 2005/0661* (2013.01); *B26B 21/225* (2013.01); *C02F 1/32* (2013.01); *C02F 2001/46133* (2013.01); *C02F 2201/46135* (2013.01); *C02F 2303/04* (2013.01); *C02F 2307/02* (2013.01)

(56) References Cited

U.S. PATENT DOCUMENTS

| | | |
|---|---|---|
| 2013/0071805 A1 | 3/2013 | Doll et al. |
| 2014/0106309 A1 | 4/2014 | Jimenez et al. |
| 2015/0017567 A1 | 1/2015 | Noack et al. |

FOREIGN PATENT DOCUMENTS

| | | |
|---|---|---|
| JP | 2002282219 | 10/2002 |
| KR | 10-1100632 B1 | 1/2012 |
| WO | WO 2005/004983 A2 | 1/2005 |
| WO | WO 2013/027954 A2 | 2/2013 |
| WO | WO 2013/043771 A1 | 3/2013 |
| WO | WO 2013/127953 A1 | 9/2013 |

ELECTROCHEMICAL DEVICE FOR RELEASING IONS

CROSS REFERENCE TO RELATED APPLICATIONS

This application is a divisional of and claims priority to U.S. patent application Ser. No. 15/533,160, filed on Jun. 5, 2017, which claims priority to the U.S. National Phase Application of PCT International Application Number PCT/EP2015/078782, filed on Dec. 7, 2015, designating the United States of America and published in the English language, which is an International Application of and claims the benefit of priority to European Patent Application No. 14196595.4, filed on Dec. 5, 2014. The disclosures of the above-referenced applications are hereby expressly incorporated by reference in their entireties.

FIELD OF THE INVENTION

The present invention relates to an electrochemical device for releasing ions, comprising an electrical circuit comprising a first electrode and a second electrode adapted for providing a galvanic cell, when the electrodes are exposed to a fluid constituting an electrolyte, and a boost converter adapted for amplifying a potential generated between the first and the second electrode. The present invention further relates to devices, such as a toothbrush or a shaver, adapted for being used in connection with a fluid, comprising such electrochemical device for releasing ions.

BACKGROUND OF THE INVENTION

Minerals and ions are extensively used and widely recognized for their positive effects on the human body. Minerals and ions may for example be used to prevent the formation of bacteria, viruses and fungal infections. The use of microcurrent are also know for purposes such as eliminating bacteria, stimulating cells of the human body or iontophoresis, which is transportation of ions in a medium and may be used for non-invasive delivery of medicine to the body. Additionally, light of various wavelengths are known to have various advantageous effects.

In recent years, we have seen that many traditional products have been redesigned or upgraded with the purpose of improving or contributing in a positive way to the health of the user. Various devices used in everyday life, such as toothbrushes or shavers, are often low-cost, expendable devices with basic functionalities. Possibilities for improving the functionality of such devices are often restricted by the need for keeping manufacturing costs as low as possible. Improvements may be directed to the direct functionality of the device, e.g. by providing new health improving functionalities, or more indirectly by improving the user experience and thereby increasing compliance and correct use.

Toothbrushes and shavers have been developed to include various functionalities based on electronics and internal power supplies. Electronic toothbrushes for example, may measure various parameters during brushing to improve brushing quality. Ionic toothbrushes incorporating a power source for controlling release of ions, and shavers incorporating battery powered vibration modules for improving shaving quality are other examples. A disadvantage related to these devices is the increase in complexity and thus, the cost of the devices.

A need exists for improving the functionality of everyday devices without considerable increasing product complexity and cost. Further, it may be advantageous to integrate health stimulation functionalities, such as ion or mineral release, into devices used extensively in everyday life.

OBJECT OF THE INVENTION

An object of the present invention is to provide simple devices that may help to improved quality of treatment and the health of the user.

In particular, it may be seen as a further object of the present invention to provide devices that are able to release ions, minerals and/or microcurrent during use, and that are relatively inexpensive to produce.

Still further, it may be seen as an object of the present invention to provide everyday devices incorporating an electrical circuit powered without the need for an integrated power source, such as a battery.

SUMMARY OF THE INVENTION

Thus, the above described object and several other objects are intended to be obtained in a first aspect of the invention by providing an electrochemical device, comprising a first part and a second part, the first part comprising: a first and a second electrode adapted for providing a galvanic cell when the first and second electrode are exposed to an external fluid, the external fluid constituting an electrolyte; one or more electrochemical systems; the galvanic cell adapted to power, when in operation, the one or more electrochemical systems; the second part comprising a boost converter adapted for amplifying a potential generated between the first electrode and the second electrode.

The external fluid is a fluid not comprised, i.e. not present in the electrochemical device.

The external fluid may be an aqueous solution comprising salts.

The external fluid may be a body fluid, such as sweat or saliva.

The one or more electrochemical systems may be an electrolytic cell and/or an electric-powered device, such as a light emitting device.

Thus, in some embodiments the one or more electrochemical system is an electric-powered device.

In some other embodiments, the one or more electrochemical system are at least two electrochemical systems.

In some further embodiments, the at least two electrochemical systems are an electrolytic cell and an electric powered device.

In some embodiments, the electric-powered device is a light emitting device or an ultrasound transducer, connected with an output side of the boost converter.

In some embodiments, the electrochemical device is an handheld device, wherein the first part is a handle portion for being held in the hand of a user, and the second part is a head portion adapted to be in contact with the external fluid.

First and second electrode are located in the first part or head portion as, in order to power the electrochemical system, the galvanic cell and thus the first and second electrode need to be exposed to an external fluid.

The first and second electrode are thus adapted to be exposed to a fluid that is provided externally, i.e. from the outside of the electrochemical device and not comprised in the electrochemical device. Accordingly, first and second electrode may be either placed on the external surface of the first part or head portion so as to be exposed to an external fluid present onto the external surface of the first part or head portion.

Thus, the above described object and several other objects are intended to be obtained in a first embodiment of the invention by providing an electrochemical device for releasing ions, comprising an electrical circuit comprising: a first electrode and a second electrode adapted for providing a galvanic cell when the electrodes are exposed to a fluid constituting an electrolyte, and a boost converter adapted for amplifying a potential generated between the first and the second electrode, wherein the electrical circuit further comprises a third electrode connected with an output side of the boost converter, the second and the third electrode, when exposed to the fluid constituting an electrolyte, being adapted for providing an electrolytic cell powered by the galvanic cell, whereby during the electrochemical processes in the galvanic cell and the electrolytic cell ions are released from one or more or the electrodes into the electrolyte.

Thus, in some embodiments the one or more electrochemical system may be an electrolytic cell provided by a third electrode connected with an output side of the boost converter and the second electrode when exposed to the external fluid constituting an electrolyte, whereby when in operation ions are released from one or more of the first, second or third electrode into the external fluid constituting an electrolyte.

As described for the first and second electrode, also the third electrode and the second electrode need to be exposed to an external fluid so as to provide an electrolytic cell. Thus first, second and third electrode are located in the first part or head portion.

The first, second and third electrode are thus adapted to be exposed to a fluid that is provided externally, i.e. from the outside of the electrochemical device and not comprised in the electrochemical device. Accordingly, first, second and third electrode may be either placed on the external surface of the first part or on the head portion so as to be exposed to an external fluid present onto the external surface of the first part or head portion.

Hereby, a self-powering electrochemical device that is able to release ions, minerals and microcurrent is provided. The electrochemical device may be implemented in a wide variety of products, some of which will be further described below. The galvanic cell and the integrated boost converter provides an output potential sufficient to power various electric-powered devices and the electrolytic process of an electrolytic cell. Hereby, by choosing suitable materials for the electrodes, ions and minerals with beneficial properties may be released by the device. Ions and minerals may be used for various purposes, e.g. in relation to the human or animal body or for cleaning or disinfection purposes. A further result of the electrochemical process is that an electrical field is created between the electrodes. Such electrical field may be used in an iontophoresis process for transportation of the released ions. Iontophoresis may for example be used for transporting charged ions into the body.

In one embodiment of the electrochemical device the first electrode may be a cathode electrode of the galvanic cell, the third electrode may be a second cathode electrode of the electrolytic cell, and the second electrode may be a common anode electrode shared by the galvanic and the electrolytic cells.

In some embodiments, the first electrode is a cathode electrode of the galvanic cell, said third electrode is a cathode electrode of the electrolytic cell, and the second electrode is a common anode electrode shared by the galvanic cell and the electrolytic cell.

In another embodiment the third electrode may constitute a second anode electrode. Further, the electrical circuit may comprise a fourth electrode constituting a second anode electrode connected with an output side of the boost converter.

In some embodiments, the fourth electrode may be a cathode.

In addition, the first electrode may comprise materials or a combination of materials chosen from gold, silver, copper, lead, tin, nickel, cobalt, iron, chromium, zinc, manganese, graphene, carbon nanotubes or fullerenes. The second electrode may comprise materials or a combination of materials chosen from lithium, rubidium, potassium, caesium, barium, strontium, calcium, sodium, magnesium, aluminium and tin. The third and fourth electrodes may comprise materials or a combination of materials chosen from any of the above mentioned groups of materials.

In the embodiment wherein the first electrode is the first cathode electrode, the first electrode may preferably comprise materials or a combination of materials chosen from gold, silver, copper, graphite or graphene, such as carbon nanotubes, the second electrode being the common anode electrode may preferably comprise materials or a combination of materials chosen from magnesium or zinc, and the third electrode being the second cathode electrode may preferably comprise materials or a combination of materials chosen from gold, silver or copper.

Additionally, the electrical circuit of the electrochemical device may comprise a light emitting device or an ultrasound transducer connected with the output side of the boost converter. Hereby, light and pulses with associated advantageous effect may be released from the device. Further, the light emitting device may be adapted for emitting light in the ultra violet spectrum suitable for killing bacteria.

As an alternative or supplement to the light emitting device or an ultrasound transducer, the electric circuit may comprise other electric-powered devices, such as a loudspeaker, connected with the output side of the boost converter. The electrical circuit may also comprise both a light emitting device and an ultrasound transducer. Also, the electrical circuit may comprise a timer-circuit for measuring time.

The boost converter of the electrochemical device described above may comprise an inductor in the form of a toroidal core inductor comprising a toroidal core made from a ferromagnetic material, and a coil.

According to a further embodiment of the invention, the above-described electrochemical device may be incorporated in a toothbrush, wherein the electrodes are provided on a brush head portion of the toothbrush and ions may be released from the electrodes into the oral cavity. Further, the electric field created by the electrodes may have certain advantageous effects, such as facilitating transportation of released ions into e.g. the teeth.

According to a still further embodiment of the invention, the above-described electrochemical device may be incorporated in a shaver comprising a shaver head portion, wherein the electrodes are provided on the shaver head portion and ions may be released from the electrodes onto the skin. Further, the electric field created by the electrodes may have certain advantageous effects, such as facilitating transportation of released ions into the skin.

According to a still further embodiment of the invention, the above-described electrochemical device may be incorporated in a bottle cap for a bottle or other type of container, wherein the electrodes are provided on an inner surface of the bottle cap and adapted for being exposed to a fluid in the bottle, whereby when the electrodes are exposed to the fluid, ions may be released from the electrodes into the fluid in the bottle.

According to a still further embodiment of the invention, the above-described electrochemical device may be incorporated in a water-cleaning device adapted for cleaning a fluid in a container, wherein the electrochemical device is arranged in a housing adapted for being at least partially submerged into a fluid, and wherein the electrodes are provided on an outer surface of the housing adapted for being submerged, whereby when the electrodes are exposed to the fluid, ions may be released from the electrodes into the fluid.

According to a still further embodiment of the invention, the above-described electrochemical device may be incorporated in a wound disinfection device for cleaning wounded skin, wherein the electrochemical device is arranged in a housing and the electrodes are provided on an exterior interface adapted for being pressed onto an area of a wounded skin, whereby when the electrodes are exposed to fluids in the wound area, ions are released from the electrodes into the fluids and the wound. Further, the electric field created by the electrodes may have certain advantageous effects, such as facilitating transportation of released ions into the skin and wound.

According to a still further embodiment of the invention, the above-described electrochemical device may be incorporated in a light band comprising a plurality of light emitting device connected with the electrical circuit, wherein the electrodes are arranged on an inner surface of the light band adapted for coming into contact with the skin of a user whereby when the electrodes are exposed to a fluid on the skin, such as perspiration, the potential created by the galvanic element powers the light emitting devices and ions are released from the electrodes.

Alternatively, the light band may comprise only the first and a second electrode arranged on the inner surface of the light band and adapted for providing a galvanic cell when the inner surface is exposed to a fluid, and the plurality of light emitting devices may be connected with an output side of the boost converter of the electrical circuit and thereby powered by the galvanic cell.

The above described object and several other objects may also be obtained in another embodiment of the invention by providing a handheld device, such as a toothbrush or a shaver, adapted for being used in connection with a fluid, the handheld device comprising: a handle portion for being held in the hand of a user, a head portion provided with a functional unit, such as a brush assembly or a razor assembly, and an electrical circuit, wherein the head portion is provided with at least a first electrode and a second electrode adapted for providing a galvanic cell when the head portion is exposed to the fluid, the first electrode and the second electrode being connected with the electrical circuit comprising a boost converter adapted for amplifying a potential generated between the first and the second electrode, and wherein the handheld device further comprises an electric-powered device, such as a light emitting device, connected with an output side of the boost converter.

According to one embodiment of the handheld device, the first electrode may be a cathode electrode and the second electrode may be an anode electrode. Further, the head portion may be provided with a third electrode connected with an output side of the boost converter, and the second and the third electrodes may be adapted for providing an electrolytic cell, when the head portion is exposed to the fluid. Additionally, the third electrode may be a second cathode electrode or alternatively a second anode electrode.

In the embodiment of the handheld device wherein the first electrode is a first cathode electrode, the first electrode may preferably comprise materials or a combination of materials chosen from gold, silver, copper, graphite or graphene, such as carbon nanotubes, the second electrode being a common anode electrode may preferably comprise materials or a combination of materials chosen from magnesium or zinc, and the third electrode being the second cathode electrode may preferably comprise materials or a combination of materials chosen from gold, silver or copper.

Further, the electric-powered device may be a light emitting device, such as an LED or an ultrasound transducer adapted for transmitting pulses. In addition, the light emitting device may be adapted for emitting light in the ultra violet spectrum suitable for killing bacteria. The handheld device may also comprise both a light emitting diode device and an ultrasound transducer. In addition, the electric-powered device may be a loudspeaker. Furthermore, the electrical circuit may comprises a timer-circuit for measuring time.

Still further, the boost converter of the handheld device may comprise an inductor in the form of a toroidal core inductor comprising a toroidal core made from a ferromagnetic material, and a coil wound around the core.

In one embodiment of the handheld device described above, the first electrode may comprise gold, silver, copper graphite or graphene, such as carbon nanotubes or fullerenes, or a combination of these, and the second electrode may comprise magnesium or zinc. Further, the third electrode may comprise silver or copper.

In one embodiment, the handheld device is a toothbrush and the head portion is a brush head of the toothbrush. In another embodiment, the handheld device is a dish brush and the head portion is a brush head of the dish brush. Further, one or more of the electrodes may be incorporated in the brush assembly of toothbrush or the dish brush.

Alternatively, the handheld device may be a shaver, wherein the head portion is a shaver head provided with one or more razor blades.

Further embodiments, advantages and features of the present invention will be apparent from and elucidated with reference to the dependent claims, the description and the accompanying drawings.

The first and other aspects and/or embodiments of the present invention may each be combined with any of the other aspects and/or embodiments. These and other aspects and/or embodiments of the invention will be apparent from and elucidated with reference to the embodiments described hereinafter.

BRIEF DESCRIPTION OF THE FIGURES

The electrochemical device and the handheld device according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1A:
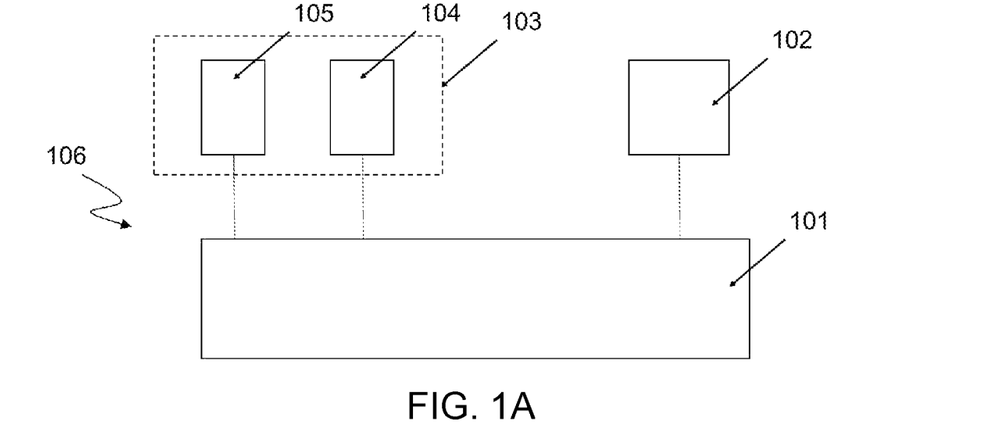
FIGS. 1A, 1B and 1C are schematic diagrams of an electrochemical device according to some embodiments of the invention.

FIG. 1A shows an electrochemical device 106 comprising a first electrode 105 and a second electrode 104 connected to a boost converter 101. The first and second electrodes being adapted for providing a galvanic cell 103 when the electrodes are exposed to an external fluid constituting an electrolyte of the galvanic cell. When the electrodes 104 and 105 are immersed in the electrolyte a potential ($V_{in}$), which may be determined an input potential, is generated between the electrodes. The input potential is amplified by the boost converter 101 to an output potential ($V_{out}$) delivered on an output side of the boost converter.

The galvanic cell 103, in the first part of the electrochemical device, is adapted to power, when in operation, an electrochemical system 102; the boost converter 101 is adapted for amplifying a potential generated between the first electrode and the second electrode.

Figure 1B:
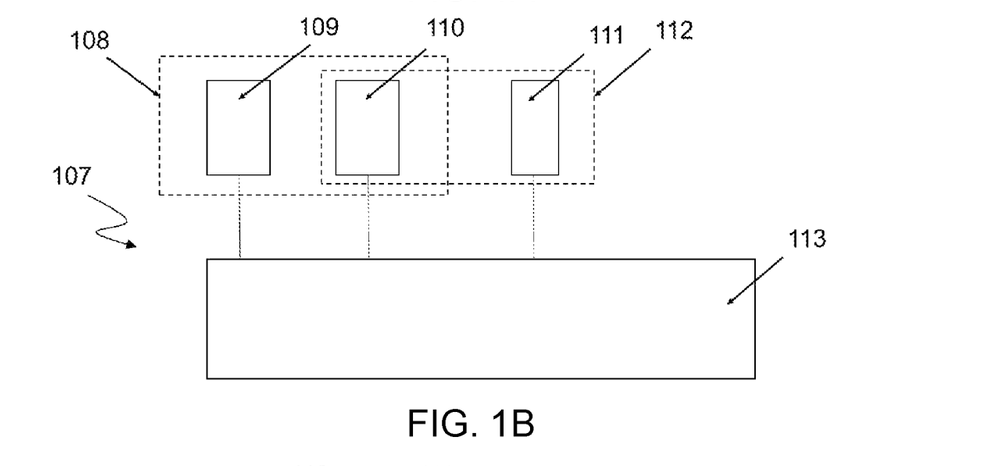

FIG. 1B shows an electrochemical device 107 comprising a first electrode 109 and a second electrode 110 connected to a boost converter 113 providing the galvanic cell 108.

In the electrochemical device 107, the electrochemical system powered by the galvanic cell 108 is the electrolytic cell 112 provided by a third electrode 111 connected with an output side of the boost converter 113 and the second electrode 110 when exposed to the external fluid constituting an electrolyte.

Figure 1C:
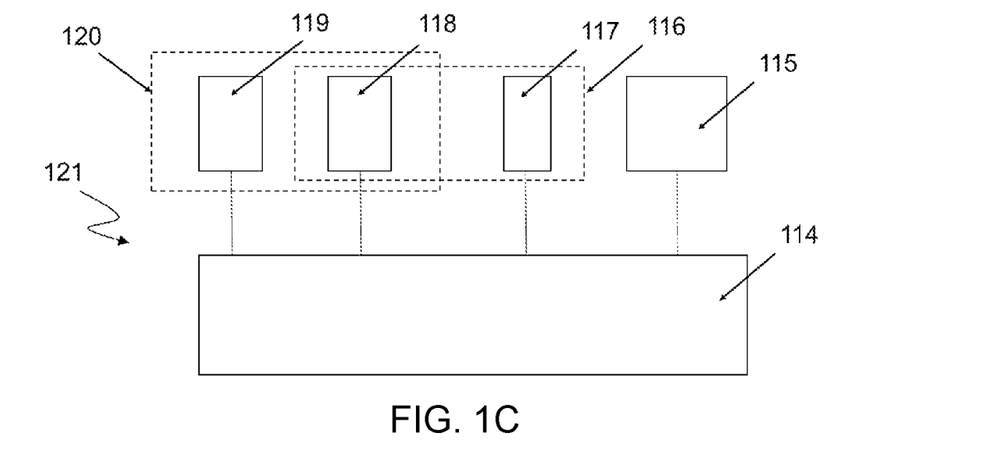

FIG. 1C shows an electrochemical device 121 comprising a first electrode 119 and a second electrode 118 connected to a boost converter 114.

In the electrochemical device 121, the galvanic cell 120 powers two electrochemical systems being an electrolytic cell 116 provided by the second electrode 118 and the third electrode 117 and an electric powered device 115 connected with an output side of the boost converter 114.

Figure 1D:
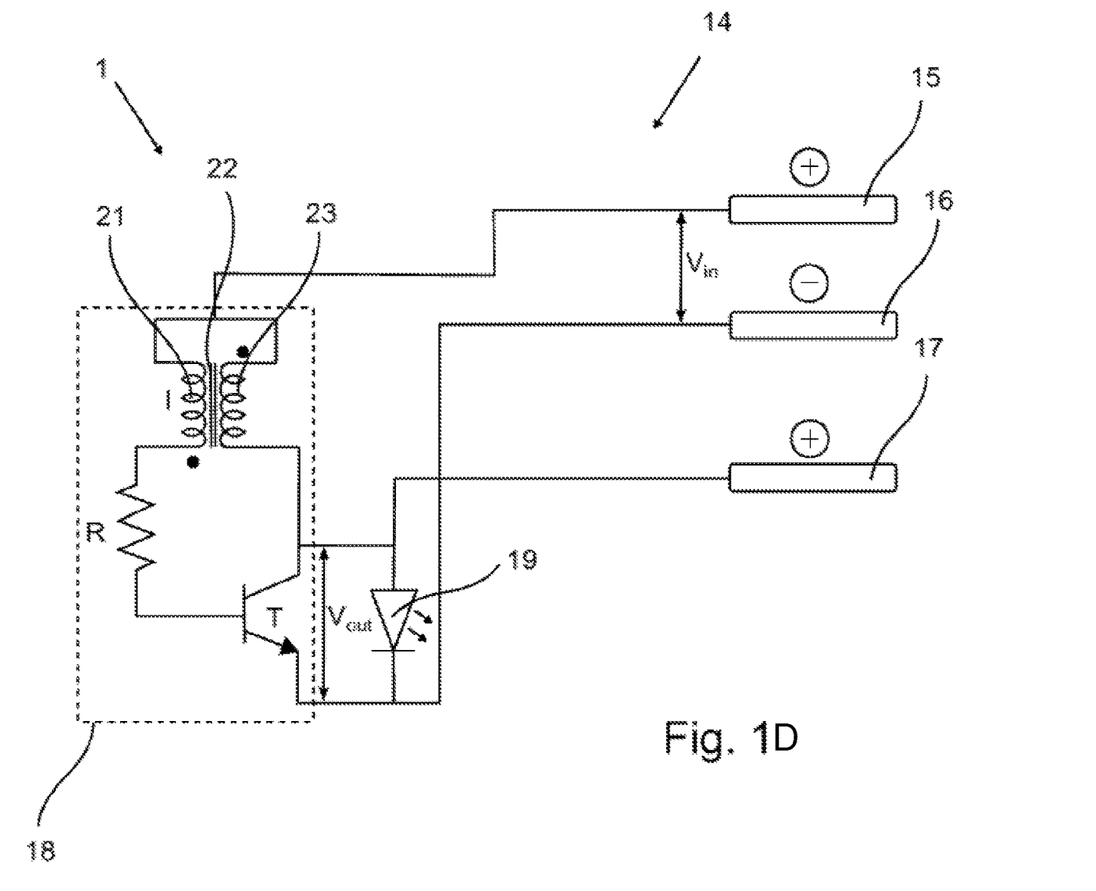
FIG. 1D is a schematic diagram of an electrical circuit of an electrochemical device according to some embodiments of the invention.

FIG. 1D shows an electrochemical device comprising an electrical circuit 14 comprising a first electrode 15 and a second electrode 16 connected to a boost converter 18. The first and second electrodes being adapted for providing a galvanic cell when the electrodes are exposed to a fluid constituting an electrolyte of the galvanic cell. When the electrodes 14, 15 are immersed in the electrolyte a potential ($V_{in}$), which may be determined an input potential, is generated between the electrodes. The input potential is amplified by the boost converter 16 to an output potential ($V_{out}$) delivered on an output side of the boost converter.

The boost converter 18 is a DC-DC converter comprising an inductor 21 and a transistor T. The inductor comprises a core 22 and a coil 23 wound around the core. The coil comprises a primary winding connected with a collector terminal of the transistor T, and a secondary winding connected with a base terminal of the transistor via a resistor R. The boost converter 18 may also be denoted a switched-mode power supply or a blocking oscillator. The first electrode is connected to the inductor and the second electrode is connected with an emitter terminal of the transistor. The boost converter 18 hereby amplifies the potential between the first and second electrodes to an output potential, $V_{out}$ of approximately 3-15 V delivered as high frequency pulses. The output side of the boost converter is defined as the collector and emitter terminals of the transistor, and the output potential is the potential between the collector and emitter of the transistor. Details about the functionality of the boost converter should be readily understood by the skilled person. Further, the boost converter may also be constructed in other ways known to the skilled person, without departing from the scope of the invention.

The output potential, $V_{out}$ delivered by the boost converter is used to power an electric-powered device 19, such as a light emitting device, an ultrasound transducer or another type of electric powered device. Subject to the materials chosen for the electrodes, the boost converter is able to amplify the potential created by the galvanic cell using tap water as an electrolyte to a level sufficient to drive a conventional light emitting diode, LED or an ultrasound transducer.

Still referring to FIG. 1D, a third electrode 17 connected with the output side of the boost converter 18 is provided as part of the electrical circuit. Together with the second electrode 16, the third electrode 17 is adapted for providing an electrolytic cell, when the electrodes are exposed to a fluid constituting an electrolyte of the electrolytic cell. The output potential, $V_{out}$ may generate an electrical current between the second and the third electrode, sufficient to drive an electrolytic process in the electrolytic cell.

Depending on the electrode material and the constituents of the fluid used as an electrolyte, various reactions may take place. According to one embodiment, materials for the electrodes are chosen such that the first electrode 15 constitutes the cathode and the second electrode 16 constitutes the anode of the galvanic cell. The first cathode electrode 15 may for example comprise gold, silver, copper, graphite or graphene, e.g. in the form of carbon nanotubes or fullerenes, or an alloy comprising one or more of these materials. The anode electrode 16 may comprise magnesium, zinc, or an alloy comprising one or more of these materials.

When the electrodes are exposed to the electrolyte, an oxidation process takes place at the anode electrode whereby positive metal ions, such as magnesium ions, are released into the fluid. During the oxidation reaction electrodes are freed and these travel to the first electrode 15 or the cathode electrode via the electrical circuit. At the cathode electrode, a reduction reaction takes place as the electrodes are absorbed by positive ions. Hereby the cathode electrode may be considered the positive side and the anode electrode the negative side of a power supply.

The electric potential created between the anode electrode and the cathode electrode of the galvanic cell is determined by the standard electrode potential of the electrode materials. Fullerenes and carbon nanotubes provides unique electrical properties and these may be used for the cathode electrode to increase the potential created between the electrodes. The maximum theoretical potential is about 2.4 V, but in practice the potential is somewhat lower and dependent on amongst others the temperature, ion concentration and resistance in the electrodes.

As described above the electrolytic reaction in the electrolytic cell is powered by the potential created in the galvanic cell. Again, dependent on the materials chosen for the electrodes, the electrolytic process may result in various metal ions such as copper ions or silver ions being released from the third electrode.

According to one embodiment, magnesium or zinc or an alloy comprising these is chosen as the material for the second electrode and silver or copper or an alloy comprising these is chosen as the material for the third electrode. With the third electrode connected to the positive side of the output side of the boost converter 18, the third electrode will constitute a cathode electrode of the electrolytic cell. In this exemplary embodiment the second electrode constitutes a common anode shared by both the galvanic cell and the electrolytic cell. During the electrolytic reaction oxidation takes place at the anode and a reduction reaction takes places at the cathode. Further, the reaction at the cathode electrode may result in the release of silver or copper ions, dependent on the material of the cathode electrode.

The composition of the electrolyte may also influence the reactions at the electrodes and the associated release of ions. Accordingly, an electrolyte with specific properties may be used to achieve specific results. In general the electrode potential and concentration of ions in a solution has an impact on the reactions which takes place and which ions that are reduce and oxidised at the cathode and the anode, respectively.

Referring to FIG. 2-5, a handheld device according to the invention will be described in further detail below. The handheld device comprises a handle portion 11 for being held in the hand of a user, and a head portion 12 extending from the handle portion. Further, the head portion is provided with a functional unit 13, such as a brush assembly 13a. A first electrode 15 and a second electrode 16 connected with an electrical circuit 14 are arranged on the head portion, adapted for providing a galvanic cell when the head portion in exposed to a fluid constituting an electrolyte. Finally, the handheld device comprises an electric-powered device 19, such as a light emitting device 19a, connected with the electrical circuit.

Figures 2A, 2B:
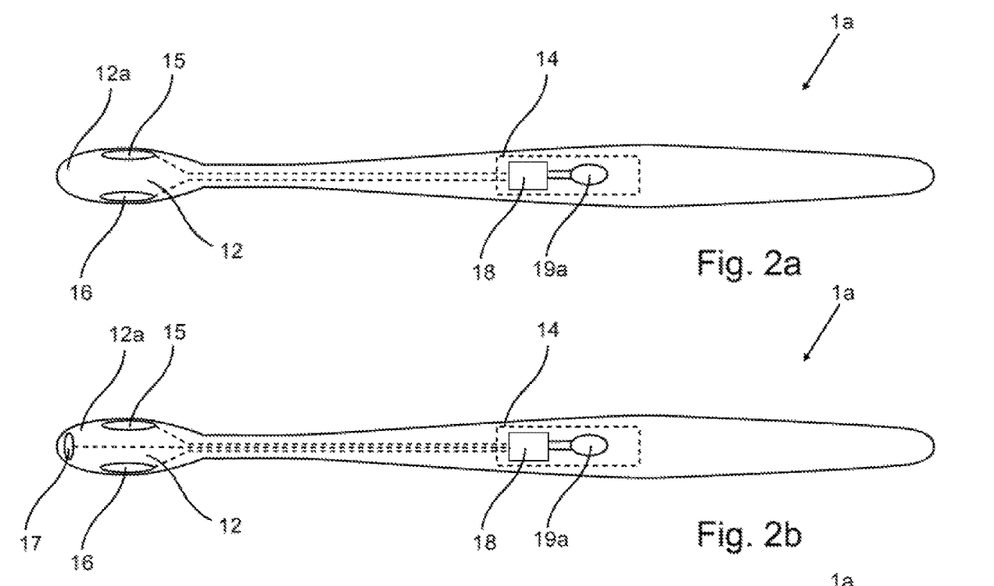
FIG. 2a-2c show different embodiments of a handheld device in the form of a toothbrush.

FIG. 2a shows a handheld device in the form of a toothbrush 1a. The toothbrush comprising a handle portion 11 and a head portion in the form of a bush head 12a provided with a functional unit in the form of a brush assembly 13a. The toothbrush further comprises an electrical circuit 14 and electrodes 15, 16 as described above. The electrodes are shown to be positioned at opposite sides of the head portion and connected to the remaining electrical circuit integrated in the handle portion 11. The electric-powered device is a light emitting device 19a which may comprise one or more light emitting diodes. The electrical circuit including the boost converter 18 and the electric-powered device may alternatively be integrated in the head portion or other parts of the toothbrush as envisaged by the skilled person.

When the toothbrush is used, the electrodes in combination with an external fluid, i.e. water, saliva and/or toothpaste create a galvanic cell as described above. The galvanic cell powers the light emitting device 19a via the boost converter 18 and light may be emitted. The light emitted may be used for both functional purposes and for guiding the user. In one embodiment the electrical circuit 14 is provided with a timer circuit (not shown) providing a timer function. The timer function measures the time the toothbrush has been used and may for example be activated when the electrodes are exposed to a fluid for the first time. When the electrodes are exposed to the fluid the light emitting device emits a light of a specific colour, e.g. red, and after a predetermined period, for example 2 minutes, the light emitted changes colour, e.g. to green. The user is thereby informed about how long the toothbrush has been used. The light emitting device may also light up to indicate that the toothbrush is properly used or as a simple gimmick for stimulating use of the toothbrush. Additionally, the electrical circuit and the light emitting device may be designed in such a way that the light emitting device only turns on during a fixed period starting from the first time the toothbrush is used. Hereby, the user may be notified when it is time to change the toothbrush. This functionality may for example be implemented by proper dimensioning of the size of the electrodes of the galvanic cell, such that the galvanic cell ceases to operate after a predetermined period of time.

In another embodiment, the light emitting device 19 may be adapted for emitting light in the ultra violet spectrum and the light emitting device may be arranged at or near the head portion 12. The ultra violet light may be used for killing bacteria either during use of the toothbrush or between uses. The light emitting device may also be adapted for emitting light having a whitening effect on the teeth.

FIG. 2b shows another embodiment which, compared to the embodiment of FIG. 2a, additionally comprises a third electrode 17. The third electrode may function as a second cathode as described above in connection with the electrochemical device.

Hereby, an electrolytic cell is created when the toothbrush is exposed to a fluid and an electrolytic process may take place. The electrolytic process may produce various ions such as copper ions or silver ions, which may have beneficial effects related to the teeth and mouth hygiene. For example, copper and silver ions may be used to fight bacteria, viruses and fungal infections. Additionally, creating negative ion, such as chloride ions or hydroxide ions may assist in removing plaque as plaque is boned to the teeth by positive ions. Further, the potential created between the electrodes create an electrical field resulting in microcurrents flowing in the electrolyte and in other parts of the oral cavity, such as in the teeth. Such microcurrents may facilitate transportation of charged ions into the teeth and other parts of the oral cavity.

Figure 2C:
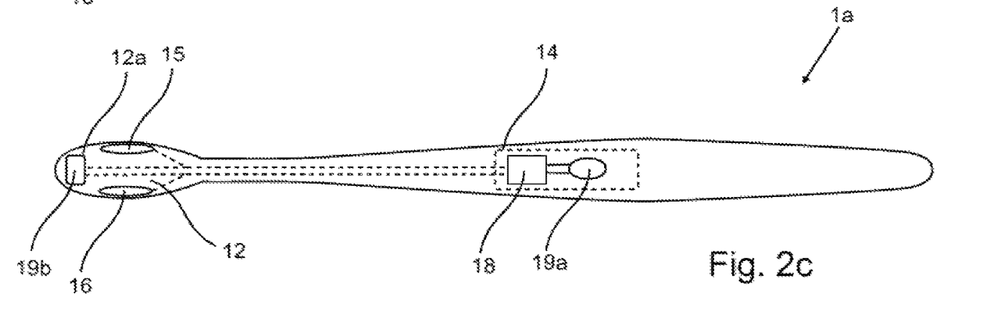

FIG. 2c shows another embodiment, which may in addition to the embodiments shown in FIGS. 2a and 2b, comprise an ultrasound transducer 19b. The ultrasound transducer is arranged at the head portion and may be used for emitting vibrations in the form of ultrasound. Emitted wavelength may be determined based on the objects to be achieved. For example, ultrasound vibrations may be used to clean the teeth by removing plaque and other impurities.

Figure 3:
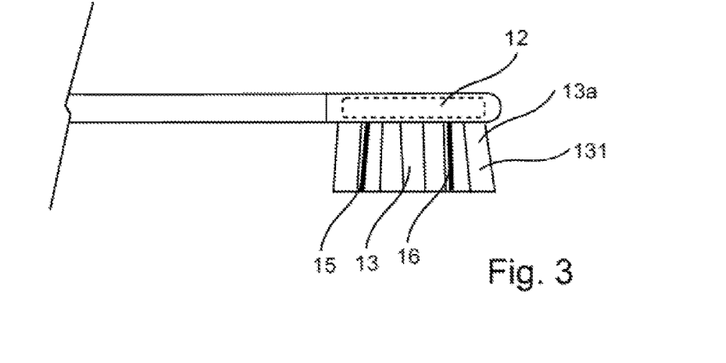
FIG. 3 shows a brushing head of the toothbrush.

FIG. 3 shows a brush head 12a, which may be a brush head of the previous disclosed embodiments. The brush head comprises a brush assembly 13a comprising a plurality of brushes 131. As shown, the electrodes may be incorporated in the bush assembly in the form of brushes 131.

Further, the toothbrush may be designed and manufactured in such a way that the brush head 12a constitutes an exchangeable and disposable part, which can be changed more frequently than the remaining parts of the toothbrush. For example, it may be advantageous to be able to change the brush head, if one or more electrodes has to be replaced. Additionally, by providing an exchangeable brush head the total live cycle cost and the carbon footprint of a toothbrush may be reduced.

Figure 4A:
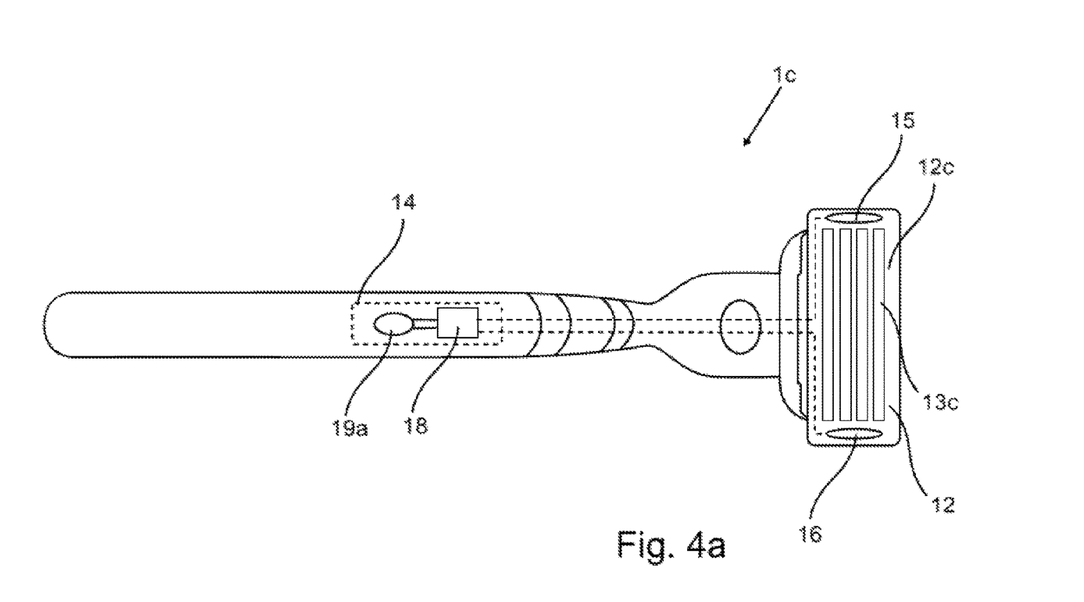
FIGS. 4a and 4b show different embodiments of a handheld device in the form of a shaver.

FIG. 4a shows a handheld device in the form of a shaver 1c. The shaver 1c comprising a handle portion 11 and a head portion in the form of a shaver head 12c provided with one or more razor blades 13c. The shaver further comprises an electrical circuit 14 and electrodes 15, 16 as described above in connection with the toothbrush. The electrodes are shown to be positioned at opposite sides of the head portion and connected to the remaining electrical circuit integrated in the handle portion 11. The electric-powered device is a light emitting device 19a, which may comprise one or more light emitting diodes. The electrical circuit including the boost converter 18 and the electric-powered device may also be integrated in the head portion or other parts of the toothbrush as envisaged by the skilled person.

When the shaver is used the electrodes come into contact with water, shaving cream and/or moisture on the skin thereby creating a galvanic cell according to the principles described above. The galvanic cell powers the light emitting device 19a via the boost converter 18 and light may be emitted. The light emitted may be used for both functional purposes and for guiding the user. The electrical circuit 14 may be provided with a timer circuit (not shown) providing a timer function as described above. The light emitting device may also light up to indicate that the shaver is properly used or for other purposes envisaged by the skilled person. As is also described above in relation to the toothbrush, the light emitting device 19 may also be adapted for emitting light in the ultra violet spectrum. Additionally, the electrical circuit and the light emitting device may be designed in such a way that the light emitting device only turns on during a fixed period starting from the first time of use of the shaver or a shaver head. Hereby, the user may be notified when it is time to change the shaver or the shaver head. This functionality may for example be implemented by dimensioning of the size of the electrodes in such a way that the galvanic cell ceases to operate after a predetermined period.

Figure 4B:
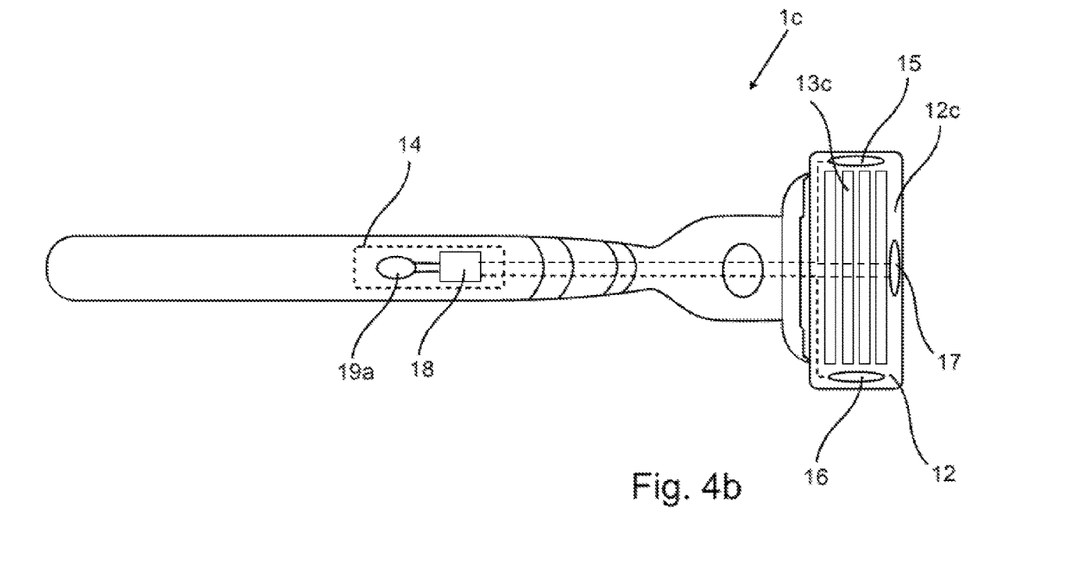

FIG. 4b shows another embodiment of a shaver which, compared to the embodiment of FIG. 4a, additionally comprises a third electrode 17. When using the shaver in connection with water, moisture on the skin and/or shaving cream an electrolytic cell and associated electrolytic reaction as described above may be created. Also as described above, the electrolytic process may produce various ions and microcurrents, which may have beneficial effects related to the skin. Further, the shaver may be designed and manufactured in such a way that the shaver head 12c constitutes an exchangeable and disposable part, which can be changed more frequently than the remaining parts of the shaver. This may for obvious reasons be advantageous, if one or more electrodes needs replacement before the remaining shaver components.

In one embodiment the shaver may also be provided with an ultrasound transducer (not shown) or other vibration module adapted for emitting vibrations. Vibrating a shaver head is a known method form improving shaving quality. According to the present invention, a vibration module may be powered by a galvanic cell using shaving cream, water and/or skin moisture as an electrolyte. Consequently, no external or integrated power supply, such as a battery, is needed.

Figure 5:
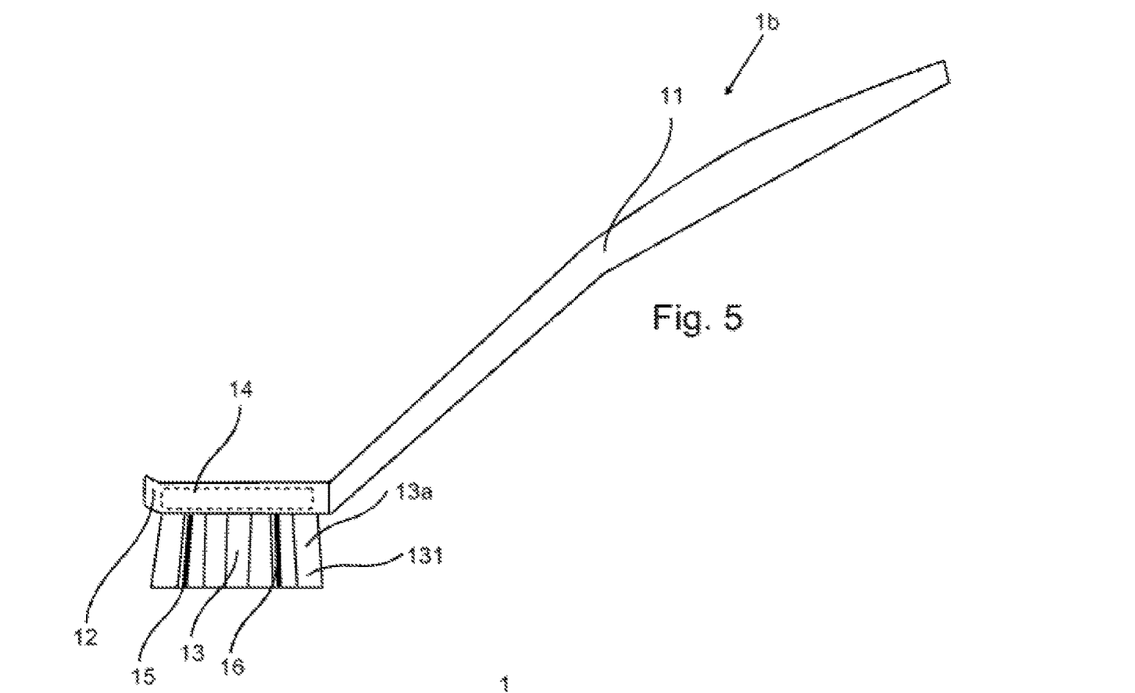
FIG. 5 shows one embodiment of a dish brush according to some embodiments of the invention.

FIG. 5 shows a handheld device in the form of a dish brush. The dish brush comprises a handle portion 11 and a head portion in the form of a bush head 12b provided with a functional unit in the form of a brush assembly 13b. The dish brush further comprises an electrical circuit 14 as indicated by the dotted square and first and second electrodes 15, 16 shown to be incorporated in the brush assembly. Here it is noted that the electrodes 15, 16 may also be incorporated in other parts of the brush head 12b as described in connection with the toothbrush embodiments. The electrical circuit may be fully or partly integrated in the handle portion. The electrical circuit comprises an electric-powered device in the form of a light emitting device 19a, which may comprise one or more light emitting diodes. The light emitting device may be arrange either in connection with the head portion or the handle portion.

The dish brush may further comprise an ultrasound transducer (not shown) or other vibration module adapted for emitting vibrations. Vibrations may be used for removing dirt or other substances, which are especially difficult to rinse off, such as burned or dried foodstuff. The ultrasound transducer or vibration module may be selectively activated by the user of simply activated when the dish brush is exposed to a fluid.

When the dish brush is used in combination with water or other fluids a galvanic cell is created according to principles described earlier. The galvanic cell powers the light emitting device 19a, and possible also the vibration module. The light emitted may be used for both functional purposes and for guiding the user. In one embodiment the electrical circuit 14 is provided with a temperature sensor (not shown) for measuring a temperature of the water used in connection with the dish brush. The temperature sensor monitors the temperature and informs the user via the light emitting device when the temperature is below or above a predefined temperature threshold. This may be done by a change in colour of the light emitted. Additionally, the electrical circuit may be provided with a timer function for measuring how long the dish brush has been used. The dish brush may also incorporate features and functions mentioned in relation to the toothbrush embodiments.

In another embodiment, the light emitting device 19 may be adapted for emitting light in the ultra violet spectrum and the light emitting device may be arranged in such a way that emitted light reaches the brush assembly 13b. The ultra violet light may be used for killing bacteria during use or between uses of the dish brush.

Figure 6:
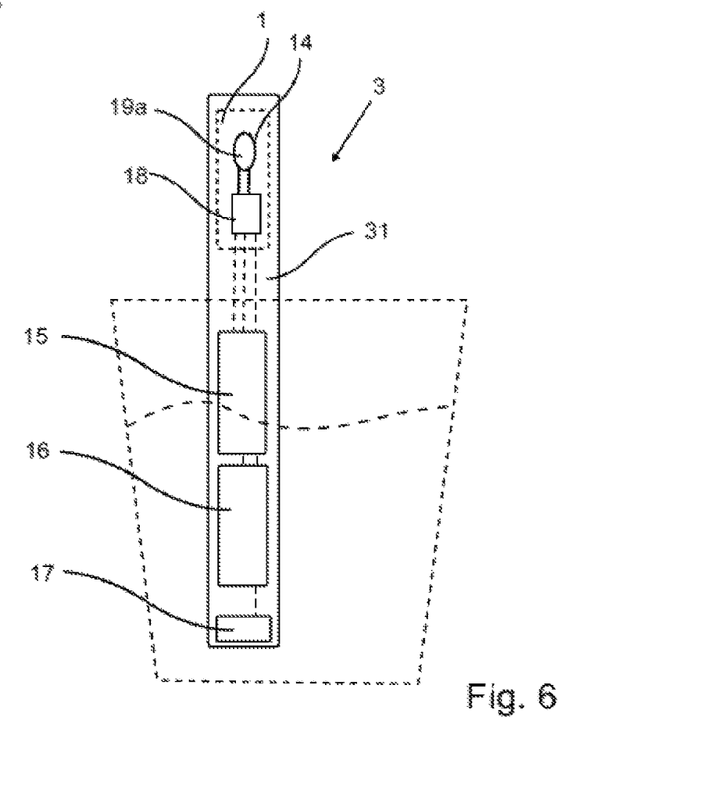
FIG. 6 shows a schematic drawing of a water-cleaning device comprising an electrochemical device.

FIG. 6 shows a water-cleaning device 3 submerged in a container containing water or possibly another fluid. The water-cleaning device integrates the electrochemical device 1 as described above, and the electrical circuit 14 is arranged in a housing 31. The housing is adapted for being submerged in water and the electrodes 15, 16, 17 of the electrochemical device are provided on an outer surface 32 of the housing. When the water-cleaning device is submerged and the electrodes are exposed to water, the galvanic and electrolytic reactions described above are initiated. Hereby, ions may be released from the electrodes into the water, which may help to kill bacteria, clean the water or enrich the water with beneficial ions and minerals.

Figure 7:
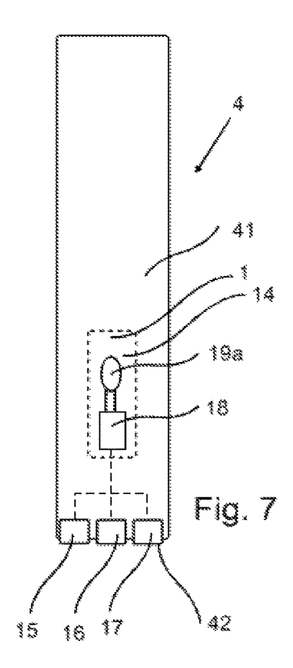
FIG. 7 shows a schematic drawing of a wound disinfection device comprising an electrochemical device.

FIG. 7 shows a wound disinfection device for cleaning wounded skin, such as an insect bite. The wound disinfection device integrates the electrochemical device 1 as described above, and the electrical circuit 14 is arranged in a housing 41. The electrodes are provided on an exterior interface 42 of the housing adapted for being pressed onto an area of a wounded skin. When the electrodes are exposed to fluids in the wound area, ions and microcurrent may be released from the electrodes into the fluids and the wound.

Figure 8:
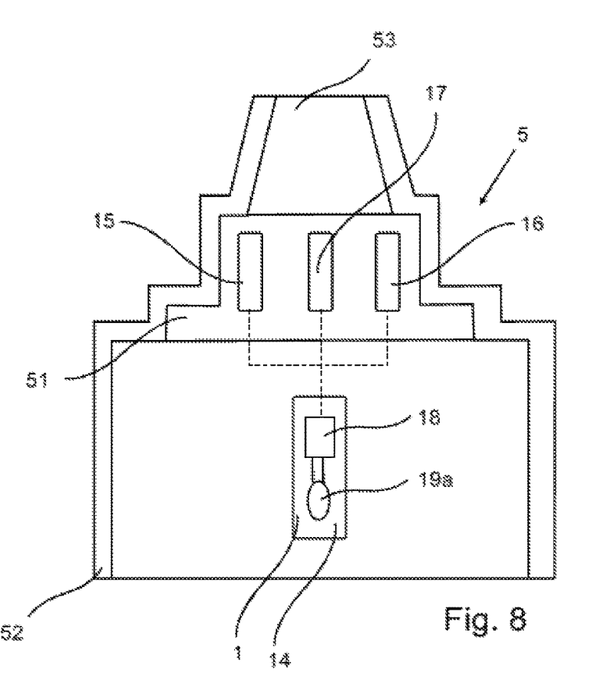
FIG. 8 shows a cross-section of a bottle cap comprising an electrochemical device.

FIG. 8 shows a cross-section of a bottle cap 5 for being mounted on a bottle. The bottle cap comprises a flange 52 for being mounted on a bottle or other containers (not shown) and a fluid passage 53 through which fluid may flow from the bottle. The bottle cap further comprises the electrochemical device 1 as described above, with the electrodes mounted in the fluid passage on an inner surface 51 of the bottle cap. Hereby, the electrodes are exposed to fluids flowing from the bottle. When the electrodes are exposed to the fluid, ions may be released into the water, which may help to kill bacteria, clean the water or enrich the water with beneficial ions and minerals.

Figure 9:
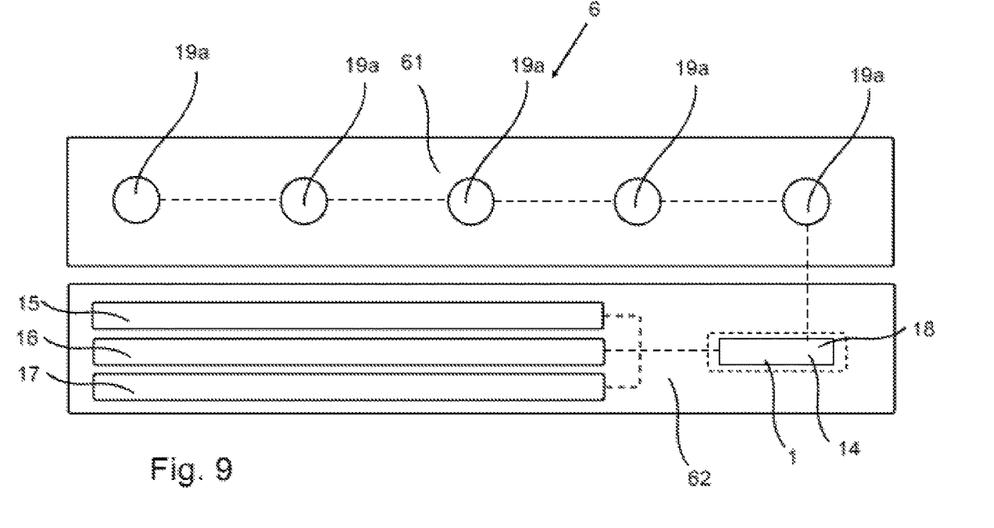
FIG. 9 shows front- and backsides of a light band comprising an electrochemical device.

FIG. 9 shows front- and backsides of a light band 6, which may be a headband or an armband adapted for being worn around the head, arm or other parts of the body. The light band may also be integrated in other wearable garments. The light band comprises the electrochemical device 1 described above and a plurality of light emitting devices 19*a* arranged on an outer surface 61 of the light band. The light emitting devices 19*a* are electrically connected with the electrical circuit 14 and the boost converter 18. The electrodes 15, 16, 17 are arranged on an inner surface 62 of the light band adapted for coming into contact with the skin of a user. Hereby, when the electrodes are exposed to fluids on the skin, such as perspiration, the light emitting devices are powered by the galvanic cell and ions may be released from the electrodes to the skin.

Although the present invention has been described in connection with the specified embodiments, it should not be construed as being in any way limited to the presented examples. The handheld device may for example also be a mobile phone or tablet, in which the galvanic cell in combination with the boost converter may be used as a backup power source or as a source for charging batteries.

The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

Items

The invention also relates to the following items:

1. An electrochemical device (1) for releasing ions, comprising an electrical circuit (14) comprising:
   a first electrode (15) and a second electrode (16) adapted for providing a galvanic cell when the electrodes are exposed to a fluid constituting an electrolyte, and
   a boost converter (18) adapted for amplifying a potential ($V_{in}$) generated between the first electrode and the second electrode,
   wherein the electrical circuit further comprises a third electrode (17) connected with an output side of the boost converter, the second electrode and the third electrode, when exposed to the fluid constituting an electrolyte, being adapted for providing an electrolytic cell powered by the galvanic cell, whereby during the electrochemical processes in the galvanic cell and the electrolytic cell ions may be released from one or more or the electrodes into the electrolyte.
2. An electrochemical device according to item 1, wherein the first electrode is a cathode electrode (15) of the galvanic cell, the third electrode is a cathode electrode of the electrolytic cell, and the second electrode is a common anode electrode (16) shared by the galvanic cell and the electrolytic cell.
3. An electrochemical device according to item 1 or 2, wherein electrical circuit further comprises a light emitting device (19*a*) or an ultrasound transducer (19*b*), connected with an output side of the boost converter.
4. An electrochemical device according to any of the previous items, wherein the boost converter comprises an inductor (21) in the form of a toroidal core inductor comprising a toroidal core (22) made from a ferromagnetic material, and a coil (23) wound around the toroidal core.
5. An electrochemical device according to any of the previous items, wherein the first electrode comprises graphene, such as carbon nanotubes or fullerenes, the anode electrode comprises magnesium or zinc, and the third electrode comprises silver or copper.
6. A toothbrush (1*a*) comprising the electrochemical device as described in any of the items 1-5, wherein the electrodes are provided on a brush head portion (12*a*) of the toothbrush, whereby when the electrodes are exposed to a fluid in the oral cavity, ions may be released from the electrodes into the oral cavity.
7. A shaver (1*c*) comprising the electrochemical device as described in any of the items 1-5, wherein the electrodes are provided on a shaver head portion (12*c*) of the shaver, whereby when the electrodes are exposed to a fluid on the skin, ions may be released from the electrodes onto the skin.
8. A bottle cap (5) for being mounted on a bottle, comprising the electrochemical device as described in any of the items 1-5, wherein the electrodes are provided on an inner surface (51) of the bottle cap arranged for being exposed to a fluid in the bottle, whereby ions may be released from the electrodes into the fluid, when the fluid passes the electrodes.
9. A water-cleaning device (3) adapted for cleaning water in a container, the water-cleaning device comprising the electrochemical device as described in any of the claim items 1-5 arranged in a housing (31) adapted for being at least partially submerged in water, wherein the electrodes are provided on an outer surface (32) of the housing adapted for being submerged, whereby when the electrodes are exposed to water, ions may be released from the electrodes into the water.
10. A wound disinfection device (4) for cleaning wounded skin, comprising an electrochemical device as described in any of the items 1-5 arranged in a housing (41), wherein the electrodes are provided on an exterior interface (42) adapted for being pressed onto an area of a wounded skin, whereby when the electrodes are exposed to fluids in the wound area, ions may be released from the electrodes into the fluids and the wound.
11. A handheld device (2), such as a toothbrush or a shaver, adapted for being used in connection with a fluid, comprising:
    a handle portion (11) for being held in the hand of a user,
    a head portion (12) provided with a functional unit (13), such as a brush assembly or a razor assembly, and
    an electrical circuit (14),
    wherein the head portion is provided with at least a first electrode (15) and a second electrode (16) adapted for providing a galvanic cell when the head portion is exposed to the fluid, the first electrode and the second electrode being connected with the electrical circuit comprising a boost converter (18) adapted for amplifying a potential ($V_{in}$) generated between the first and the second electrode, and wherein the handheld device further comprises an electric-powered device (19), such as a light emitting device (19a), connected with an output side of the boost converter.

12. A handheld device according to item 11, wherein the first electrode is a cathode electrode (15) and the second electrode is an anode electrode (16) of the galvanic cell.

13. A handheld device according to item 11 or 12, wherein the electric-powered device is a light emitting device (19a) or and ultrasound transducer (19b) adapted for transmitting pulses.

14. A handheld device according to any of the items 11-13, wherein the handheld device is a toothbrush (1a) and the head portion is a brush head (12a) of the toothbrush.

15. A handheld device according to any of the items 11-14, wherein the head portion is provided with a third electrode (17) connected with an output side of the boost converter, and the second and the third electrodes are adapted for providing an electrolytic cell when the head portion is exposed to the fluid.

The invention also relates to the following items and embodiments according to the first aspect of the invention and its embodiments:

16. An electrochemical device according to first aspect of the invention and its embodiments, wherein the first electrode comprises graphene, such as carbon nanotubes or fullerenes, the second electrode comprises magnesium or zinc, and said third electrode comprises silver or copper.

17. An electrochemical device according to first aspect of the invention and its embodiments, wherein the electrochemical device is a toothbrush and wherein the first, second and third electrodes are provided on a brush head portion of the toothbrush, whereby when the electrodes are exposed to the external fluid in the oral cavity, ions may be released from the electrodes into the oral cavity.

18. An electrochemical device according to first aspect of the invention and its embodiments, wherein the electrochemical device is a shaver and wherein the first, second and third electrodes are provided on a shaver head portion of the shaver, whereby when the electrodes are exposed to the external fluid on the skin, ions may be released from the electrodes onto the skin.

19. An electrochemical device according to first aspect of the invention and its embodiments, wherein said electrochemical device is a bottle cap for being mounted on a bottle and wherein said first, second and third electrodes are provided on an inner surface of said bottle cap arranged for being exposed to said external fluid in said bottle, whereby when the electrodes are exposed to said external fluid in said bottle, ions may be released from the electrodes into said external fluid in said bottle.

20. An electrochemical device according to first aspect of the invention and its embodiments, wherein said electrochemical device is a water-cleaning device adapted for cleaning water in a container, wherein said first, second and third electrodes are arranged in a housing adapted for being at least partially submerged in water, wherein said first, second and third electrodes are provided on an outer surface of said housing adapted for being submerged, whereby when the electrodes are exposed to said external fluid, such as water, ions may be released from the electrodes into said external fluid.

21. An electrochemical device according to first aspect of the invention and its embodiments, wherein said electrochemical device is a wound disinfection device for cleaning wounded skin, wherein said first, second and third electrodes are arranged in a housing and wherein said first, second and third electrodes are provided on an exterior interface adapted for being pressed onto an area of a wounded skin, whereby when the electrodes are exposed to said external fluids located in the wound area, ions may be released from the electrodes into said external fluids in the wound area.

22. An electrochemical device according to first aspect of the invention and its embodiments, wherein said electric-powered device is a light emitting device, connected with an output side of said boost converter.

23. An electrochemical device according to first aspect of the invention and its embodiments, further comprising an electrical circuit;
wherein said handheld device is adapted for being used in connection with said external fluid, wherein said head portion is provided with a functional unit, wherein said head portion is provided with at least said first electrode and said second electrode adapted for providing said galvanic cell when said head portion is exposed to said external fluid, said first electrode and said second electrode being connected with said electrical circuit comprising said boost converter adapted for amplifying a potential ($V_{in}$) generated between said first and said second electrode, and wherein said handheld device further comprises said electric-powered device, such as a light emitting device, connected with an output side of said boost converter.

24. An electrochemical device according to first aspect of the invention and its embodiments, wherein said functional unit is a brush assembly or a razor assembly.

25. An electrochemical device according to first aspect of the invention and its embodiments, wherein the electric-powered device is a light emitting device or and ultrasound transducer adapted for transmitting pulses.

26. An electrochemical device according to first aspect of the invention and its embodiments, wherein said handheld device is a toothbrush and said head portion is a brush head of the toothbrush.

27. An electrochemical device according to first aspect of the invention and its embodiments, wherein said head portion is provided with said third electrode connected with an output side of said boost converter, and said second and said third electrodes are adapted for providing an electrolytic cell when said head portion is exposed to said external fluid.

The invention claimed is:

1. An electrochemical device, comprising a first part and a second part,
said first part comprising:
a first and a second electrode adapted for providing a galvanic cell when said first and second electrode are exposed to an external fluid, said fluid constituting an electrolyte,
one or more electrochemical system;
said galvanic cell adapted to power, when in operation, said one or more electrochemical system; and
said second part comprising a boost converter adapted for amplifying a potential generated between said first electrode and said second electrode;

wherein said one or more electrochemical system are an electrolytic cell provided by a third electrode connected with an output side of said boost converter and said second electrode when exposed to said external fluid constituting an electrolyte, whereby when in operation ions are released from one or more of said first, second or third electrode into said external fluid constituting an electrolyte; and wherein said one or more electrochemical system are at least two electrochemical systems.

2. The electrochemical device according to claim 1, wherein said electrochemical device is a handheld device, wherein said first part is a handle portion for being held in the hand of a user, and said second part is a head portion adapted to be in contact with said external fluid.

3. The electrochemical device according to claim 1, wherein said first electrode is a cathode electrode of said galvanic cell, said third electrode is a cathode electrode of said electrolytic cell, and said second electrode is a common anode electrode shared by said galvanic cell and said electrolytic cell.

4. The electrochemical device according to claim 1, wherein said at least two electrochemical systems are an electrolytic cell and an electric powered device.

5. The electrochemical device according to claim 1, wherein said device is a light emitting device or an ultrasound transducer, connected with an output side of the boost converter.

6. The electrochemical device according to claim 1, wherein said boost converter comprises an inductor in the form of a toroidal core inductor comprising a toroidal core made from a ferromagnetic material, and a coil wound around the toroidal core.

7. The electrochemical device according to claim 1, wherein said first electrode comprises graphene, carbon nanotubes or fullerenes, said second electrode comprises magnesium or zinc, and said third electrode comprises silver or copper.

8. The electrochemical device according to claim 1, wherein said electrochemical device is a toothbrush and wherein said first, second and third electrodes are provided on a brush head portion of the toothbrush, whereby when said electrodes are exposed to said external fluid in the oral cavity, ions may be released from the electrodes into the oral cavity.

9. The electrochemical device according to claim 1, wherein said electrochemical device is a shaver and wherein said first, second and third electrodes are provided on a shaver head portion of the shaver, whereby when the electrodes are exposed to said external fluid on the skin, ions may be released from the electrodes onto the skin.

10. The electrochemical device according to claim 1, wherein said electrochemical device is a bottle cap for being mounted on a bottle and wherein said first, second and third electrodes are provided on an inner surface of said bottle cap arranged for being exposed to said external fluid in said bottle, whereby when the electrodes are exposed to said external fluid in said bottle, ions may be released from the electrodes into said external fluid in said bottle.

11. The electrochemical device according to claim 1, wherein said electrochemical device is a water-cleaning device adapted for cleaning water in a container, wherein said first, second and third electrodes are arranged in a housing adapted for being at least partially submerged in water, wherein said first, second and third electrodes are provided on an outer surface of said housing adapted for being submerged, whereby when the electrodes are exposed to said external fluid, ions may be released from the electrodes into said external fluid.

12. The electrochemical device according to claim 3, wherein said electrochemical device is a wound disinfection device for cleaning wounded skin, wherein said first, second and third electrodes are arranged in a housing and wherein said first, second and third electrodes are provided on an exterior interface adapted for being pressed onto an area of a wounded skin, whereby when the electrodes are exposed to said external fluids located in the wound area, ions may be released from the electrodes into said external fluids in the wound area.

13. The electrochemical device according to claim 4, wherein said electric-powered device is a light emitting device, connected with an output side of said boost converter.

14. The electrochemical device according to claim 4, further comprising an electrical circuit; wherein said handheld device is adapted for being used in connection with said external fluid, wherein said head portion is provided with a functional unit, wherein said head portion is provided with at least said first electrode and said second electrode adapted for providing said galvanic cell when said head portion is exposed to said external fluid, said first electrode and said second electrode being connected with said electrical circuit comprising said boost converter adapted for amplifying a potential generated between said first and said second electrode, and wherein said handheld device further comprises said electric-powered device, or a light emitting device, connected with an output side of said boost converter.

15. The electrochemical device according to claim 4, further comprising an electrical circuit; wherein said handheld device is adapted for being used in connection with said external fluid, wherein said head portion is provided with a functional unit, wherein said head portion is provided with at least said first electrode and said second electrode adapted for providing said galvanic cell when said head portion is exposed to said external fluid, said first electrode and said second electrode being connected with said electrical circuit comprising said boost converter adapted for amplifying a potential generated between said first and said second electrode, and wherein said handheld device further comprises said electric-powered device, or a light emitting device, connected with an output side of said boost converter, wherein said functional unit is a brush assembly or a razor assembly.

16. The electrochemical device according to claim 4, further comprising an electrical circuit; wherein said handheld device is adapted for being used in connection with said external fluid, wherein said head portion is provided with a functional unit, wherein said head portion is provided with at least said first electrode and said second electrode adapted for providing said galvanic cell when said head portion is exposed to said external fluid, said first electrode and said second electrode being connected with said electrical circuit comprising said boost converter adapted for amplifying a potential generated between said first and said second electrode, and wherein said handheld device further comprises said electric-powered device, or a light emitting device, connected with an output side of said boost converter, wherein the electric-powered device is a light emitting device or an ultrasound transducer adapted for transmitting pulses.

17. The electrochemical device according to claim 14, wherein said handheld device is a toothbrush and said head portion is a brush head of the toothbrush.

* * * * *